(12) United States Patent
Tschritter

(10) Patent No.: US 9,086,382 B2
(45) Date of Patent: Jul. 21, 2015

(54) METHOD FOR DETERMINING SULFUR CONTENT IN FIBERS

(75) Inventor: Jonathan Samuel Tschritter, Chesterfield, VA (US)

(73) Assignee: E I DUPONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 14/371,794

(22) PCT Filed: Jan. 11, 2012

(86) PCT No.: PCT/US2012/020892
§ 371 (c)(1),
(2), (4) Date: Jul. 11, 2014

(87) PCT Pub. No.: WO2013/105947
PCT Pub. Date: Jul. 18, 2013

(65) Prior Publication Data
US 2015/0029506 A1      Jan. 29, 2015

(51) Int. Cl.
*G01J 3/30* (2006.01)
*G01N 21/73* (2006.01)
*G01N 31/12* (2006.01)
*G01N 33/44* (2006.01)

(52) U.S. Cl.
CPC . *G01N 21/73* (2013.01); *G01J 3/30* (2013.01); *G01N 31/12* (2013.01); *G01N 33/44* (2013.01)

(58) Field of Classification Search
CPC ......... G01N 21/73; G01N 21/68; G01J 3/443; H01J 49/105; H05H 1/30
USPC .......................................................... 356/316
See application file for complete search history.

(56) References Cited

U.S. PATENT DOCUMENTS 3,973,911 A * 8/1976 Von Smolinski et al. ...... 436/122
2013/0196445 A1 * 8/2013 Kinoshiro et al. ............ 436/123

* cited by examiner

*Primary Examiner* — Tarifur Chowdhury
*Assistant Examiner* — Md Rahman

(57) ABSTRACT

The invention concerns methods for measuring sulfur content in a fiber or polymer resin sample comprising: a) contacting the sample with a solution comprising sodium hydroxide to convert sulfur to sodium sulfate, b) combusting the sample of step a) in a furnace to remove essentially all organic materials to produce a residue; c) dissolving the residue in concentrated nitric acid; and d) determining the sulfur content of the sample using ICP Emission Spectrometry.

4 Claims, No Drawings

METHOD FOR DETERMINING SULFUR CONTENT IN FIBERS

TECHNICAL FIELD

The invention concerns methods of determining sulfur content in organic fibers and polymer resins.

BACKGROUND

Advances in polymer chemistry and technology over the last few decades have enabled the development of high-performance polymeric fibers. For example, liquid-crystalline polymer solutions of rigid-rod polymers can be formed into high strength fibers by spinning liquid-crystalline polymer solutions into dope filaments, removing solvent from the dope filaments, washing and drying the fibers; and if desired, further heat treating the dried fibers to increase tensile properties. One example of high-performance polymeric fibers is para-aramid fiber such as poly(paraphenylene terephthalamide) ("PPD-T" or "PPTA").

Many other examples of polymers capable of producing high-performance fibers are known and many such polymers and copolymers are soluble in concentrated sulfuric acids. A common solvent like sulfuric acid is a preferred solvent for achieving liquid crystalline concentrations of such polymers and provides fiber manufacturing processes with attractive economics. The processing of polymers from sulfuric acid solutions, however, can result in residual amounts of sulfur being left in the processed fibers in the form of undesirable impurities or incorporation into the polymer itself.

It has been determined that removal of sulfur in as spun or intermediate fibers processed from sulfuric acid can improve certain yarn physical properties, and thus accurate methods for determining sulfur content are desirable. An accurate determination of sulfur content in fibers, however, is difficult. In some cases, especially at low sulfur concentrations, traditional combustion/gas chromatography may lack precision and or reproducibility and require more sample measurements for improved confidence. As such, an improved method is needed in the art.

SUMMARY

In some aspects, the invention concerns methods for measuring sulfur content in a fiber or polymer resin sample comprising: a) contacting the sample with a solution comprising sodium hydroxide to convert sulfur to sodium sulfate, b) combusting the sample of step a) in a furnace to remove essentially all organic materials to produce a residue; c) dissolving the residue in concentrated nitric acid; and d) determining the sulfur content of said sample using ICP Emission Spectrometry.

In certain embodiments, a 0.01 to 1 N aqueous solution of sodium hydroxide is used in step a). Some embodiments, comprise the additional step in that prior to step b), the sample of step a) is heated to remove at least a portion of residual liquid from said sample.

DETAILED DESCRIPTION OF ILLUSTRATIVE EMBODIMENTS

The present invention may be understood more readily by reference to the following detailed description taken in connection with the accompanying figures and examples, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention.

Fiber or polymer resin samples may be placed in any suitable container for treatment with dilute base. Such containers should be ones that do not contaminate the samples in a manner that interferes with obtaining an accurate sulfur content measurement. One suitable container is a quartz crucible.

An amount of fiber or polymer resin suitable for producing a sample sufficient to be analyzed by ICP should be used. In some embodiments, 0.3 to 0.6 grams of sample is used. This method is especially useful for better precision measurement of the sulfur content of samples having a sulfur content of 1 weight percent or less, preferably 0.1 weight percent or less, and especially for samples having a sulfur content of 0.05 weight percent or less.

Dilute base is added to the fiber sample in the container such that the sample is preferably covered with the solution. In some embodiments, the sample is covered with a minimum amount of solution so as minimize the liquid that must be evaporated in a further step. Any solution concentration that converts substantially all of the sulfur content of the sample to sodium sulfate may be utilized. In some embodiments, a 0.01 to 1 N sodium hydroxide solution is utilized. One preferred embodiment uses a 0.1 N sodium hydroxide solution. The sample is immersed in the sodium hydroxide solution for a time sufficient to convert the sulfur content in the fiber sample to sodium sulfate; this time is preferably 15 minutes or greater. While not wanting to be bound by theory, it is believed the treatment of the sample with base in this manner inhibits the volatilization and loss of sulfur during ashing.

The container comprising the fiber or polymer resin sample and the dilute base solution can be heated until a substantial portion of the liquid is evaporated. Preferably, substantially all of the liquid is evaporated. A hot plate or other heat source may be used for the evaporation. In a preferred embodiment, the liquid is slowly evaporated. In some preferred embodiments, a time of 10 minutes to one hour is required. In one embodiment, evaporation takes about 30 minutes.

The dried fiber or polymer resin sample is then ashed. Any suitable method of combustion may be utilized for the ashing. In some embodiments, a muffle furnace, such as a Thermolyne 62770 Furnace may be utilized. In some embodiments, the furnace is set to a temperature of 400-800 degrees C. In one embodiment a temperature of about 600 degrees C. is used. The ashing should occur for a time to allow substantially complete ashing. In some embodiments, the time is 2-10 hours. In one embodiment, the time is about 5 hours.

After ashing, the resulting sample is contacted with concentrated nitric acid (preferably commercial grade) and the resulting mixture is then diluted with purified water (such as Milli-Q Water) to produce a sample suitable for ICP analysis. In some embodiments, a ratio of 20:1 to 5:1 water to acid is used. In one preferred embodiment, 2 grams of nitric acid and 25 grams of water are used.

The resulting solution can then be transferred from the container to a centrifuge tube and then analyzed in the axial mode by ICP Emission Spectrometer. The results are calibrated using a blank, such as a 10 ppm Sulfur Standard, and a 100 ppm Sulfur standard. Such standards may be obtained from High Purity Standards located in Charleston, S.C.

Inductively Coupled Plasma (ICP) Emission Spectrometry is well known in the art as a tool for detection and quantification of trace metals in a sample. The method utilizes inductively coupled plasma which produces excited atoms and ions. These excited atoms and ions emit electromagnetic radiation at wavelengths that are characteristic for a particular element. Based on the intensity of the emission, the concentration of the element within the sample can be determined by comparison with samples of known concentration. One suitable instrument for performing this analysis is the Perkin Elmer 5400 DV ICP Emission Spectrometer.

As used in the specification including the appended claims, the singular forms "a," "an," and "the" include the plural, and reference to a particular numerical value includes at least that particular value, unless the context clearly dictates otherwise. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable. When any variable occurs more than one time in any constituent or in any formula, its definition in each occurrence is independent of its definition at every other occurrence. Combinations of substituents and/or variables are permissible only if such combinations result in stable compounds.

The invention is illustrated by the following examples, which are not intended to be limiting in nature.

Test Methods

Sulfur by Combustion using Thermoscientific FLASH 2000 Automatic Elemental Analyzer (a Conventional Test Method).

In this test method, percent sulfur is determined by combustion and is measured according to ASTM D4239 Method B. A carefully weighed amount of sample (typically 2.5-4.5 mg) and of vanadium pentoxide accelerant (typically 10 mg) is placed in a tin capsule. The capsule is then dropped into an oxidation/reduction reactor kept at a temperature of 900-1000° C. The exact amount of oxygen required for optimum combustion of the sample is delivered into the combustion reactor at a precise time. The exothermic reaction with oxygen raises the temperature to 1800° C. for a few seconds. At this high temperature both organic and inorganic substances are converted into elemental gases which, after further reduction (to nitrogen, carbon dioxide, water and sulfur dioxide), are separated in a chromatographic column and finally detected by a highly sensitive thermal conductivity detector (TCD).

Typical Running Conditions for Carbon, Hydrogen, Nitrogen, and Sulfur (CHNS):

| Method setpoints | CHNS |
| --- | --- |
| Left Furnace (° C.) | 950 |
| Oven (° C.) | 75 |
| Carrier (ml/min) | 140 |
| Oxygen (ml/min) | 250 |
| Reference (ml/min) | 150 |
| Cycle (Run Time) (sec) | 480 |
| Sampling Delay (sec) | 12 |
| Oxygen Injection End (sec) | 5 |

Four samples of BBOT ((5-tert-butyl-benzoxazol-2-yl) thiophene. C=72.53% H=6.09% N=6.51% S=7.44%) standard for sulfur are run to develop the calibration curve. Once the calibration curve is verified, samples are analyzed.

The operation of a High Temperature Tube Furnace is described in ASTM D4239-10: "Sulfur in the Analysis Sample of Coal and Coke Using High Temperature Tube Furnace Combustion."

Inventive Test Method

A clean 100-mL Quartz crucible is placed on a 4 decimal place analytical balance and the balance is zeroed. Between 0.3 g-0.6 g of fiber or polymer resin is weighed into the crucible. Small amounts of 0.1 N sodium hydroxide are carefully added to the fiber or polymer resin sample until it is covered with the solution. The sample is allowed to set in the solution for 15 minutes. The fiber or polymer resin is heated on a hotplate at a temperature of 190 deg C. The solution is allowed to slowly evaporate. This step usually takes about 30 minutes. After the solution has completely evaporated in the 100-mL crucible, the crucible is placed in a muffle furnace set at a temperature of 600 deg C. The sample is allowed to ash for 5 hours. After the 5 hour ashing time, the crucible is removed from the muffle furnace and allowed to cool for 30 minutes. 2 mL of concentrated environmental grade nitric acid is added to the 25-mL graduated cylinder and the cylinder is then filled to the 25 mL mark with Milli-Q Water. The acid solution is transferred from the 25-mL graduated cylinder to the 100-mL crucible containing the ashed material. As soon as the acid solution is added, the ash immediately dissolves. The acid solution is transferred from the 100-mL crucible to a 15-mL plastic centrifuge tube. The acid solution is then analyzed in the axial mode by a Perkin Elmer 5400 DV ICP Emission Spectrometer using the 181.975 nm Sulfur Emission line. The ICP Emission Spectrometer is calibrated using a blank, a 10 ppm Sulfur Standard, and a 100 ppm Sulfur standard. The ICP standards were prepared by High Purity Standards located in Charleston, S.C.

EXAMPLES

Sulfur content was determined by ICP (the inventive method) and standard combustion method (the conventional method) for 8 fiber samples. Each fiber sample comprises polymer derived from the copolymerization of 5(6)-amino-2-(p-aminophenyl)benzimidazole (DAPBI), para-phenylenediamine (PPD) and terephthaloyl dichloride (TCl) These results are reported in Table 1 below.

TABLE 1

Sulfur content determinations

| Item | Measured ppm of Sulfur ICP Method | Measured ppm of Sulfur Combustion |
| --- | --- | --- |
| 1 | 833 | 0 |
| 2 | 690 | 1200/0* |
| 3 | 1870 | 0/1300* |
| 4 | 69 | 0 |
| 5 | 5530 | 4970 |
| 6 | 1480 | 710 |
| 7 | 1530 | 710 |
| 8 | 1430 | 710 |

*Repeats

What is claimed:

1. A method of measuring sulfur content in a fiber or polymer resin sample comprising the following steps, in order:
   a) contacting said sample with a solution comprising sodium hydroxide to convert said sulfur to sodium sulfate,
   b) combusting the sample of step a) in a furnace to remove essentially all organic materials to produce a residue;
   c) dissolving said residue of step b) in concentrated nitric acid; and d) determining the sulfur content of the residue in concentrated nitric acid of step c) using Inductively Coupled Plasma (ICP) Emission Spectrometry to excite atoms and ions in the sample to emit electromagnetic radiation, and then comparing the intensity of emission using a sulfur emission line to that of samples of known concentration.

2. The method of claim 1, where said solution comprising sodium hydroxide is an aqueous solution having a sodium hydroxide content in the range of from 0.01 to 1 N.

3. The method of claim 1, wherein prior to step b), the fiber or polymer resin sample of step a) is heated to remove at least a portion residual liquid from said sample.

4. The method of claim 1, wherein said fiber or polymer resin sample is soluble in concentrated sulfuric acid.

\* \* \* \* \*